(12) United States Patent
Wang

(10) Patent No.: US 8,518,094 B2
(45) Date of Patent: Aug. 27, 2013

(54) PRECISELY GUIDED PHOTOTHERAPY APPARATUS

(75) Inventor: Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 161 days.

(21) Appl. No.: 13/037,397

(22) Filed: Mar. 1, 2011

(65) Prior Publication Data

US 2011/0218597 A1   Sep. 8, 2011

Related U.S. Application Data

(60) Provisional application No. 61/309,671, filed on Mar. 2, 2010.

(51) Int. Cl.
*A61N 5/067* (2006.01)

(52) U.S. Cl.
USPC .......................................................... 607/89

(58) Field of Classification Search
CPC ...................................................... A61N 5/067
USPC ........................................................... 607/89
See application file for complete search history.

(56) References Cited

U.S. PATENT DOCUMENTS

| | | | | |
|---|---|---|---|---|
| 4,718,416 A | * | 1/1988 | Nanaumi | 606/9 |
| 4,928,695 A | * | 5/1990 | Goldman et al. | 600/374 |
| 5,409,481 A | * | 4/1995 | Poppas et al. | 606/12 |
| 5,820,553 A | * | 10/1998 | Hughes | 600/426 |
| 5,860,967 A | * | 1/1999 | Zavislan et al. | 606/9 |
| 5,928,221 A | * | 7/1999 | Sasnett et al. | 606/5 |
| 5,959,725 A | * | 9/1999 | Ghosh | 356/121 |
| 6,123,719 A | * | 9/2000 | Masychev | 600/407 |
| 6,267,779 B1 | * | 7/2001 | Gerdes | 607/89 |
| 6,312,451 B1 | * | 11/2001 | Streeter | 607/89 |
| 6,413,267 B1 | * | 7/2002 | Dumoulin-White et al. | 607/89 |
| 6,436,127 B1 | * | 8/2002 | Anderson et al. | 607/89 |
| 6,556,858 B1 | * | 4/2003 | Zeman | 600/473 |
| 6,641,578 B2 | * | 11/2003 | Mukai | 606/9 |
| 6,690,964 B2 | * | 2/2004 | Bieger et al. | 600/424 |
| 6,790,205 B1 | * | 9/2004 | Yamazaki et al. | 606/9 |
| 6,887,233 B2 | * | 5/2005 | Angeley et al. | 606/17 |
| 6,935,748 B2 | * | 8/2005 | Kaufman et al. | 353/28 |
| 6,984,228 B2 | * | 1/2006 | Anderson et al. | 606/9 |
| 6,984,288 B2 | * | 1/2006 | Dhindsa et al. | 156/345.47 |

(Continued)

FOREIGN PATENT DOCUMENTS

WO    WO 0178830 A2 * 10/2001

OTHER PUBLICATIONS

Roundy C.B., Current Technology of Laser Beam Profile Measurements, Spiricon Inc., 1995.*

(Continued)

*Primary Examiner* — Sam Yao
*Assistant Examiner* — Manolis Pahakis

(57) ABSTRACT

A precisely guided phototherapy apparatus for treating soft tissue injury, chronic pain, and promoting wound healing for both human and animal targets. The phototherapy apparatus comprises sensors for monitoring the intensity, position, and movement of the therapeutic light beam over the treatment area. The delivered light energy dosage is determined accordingly based on these parameters. The phototherapy apparatus further comprises a projector device for projecting markers on top of the treatment area. The markers represent the values of the delivered light energy dosage for assisting the practitioner or clinician in precisely controlling the phototherapy procedure.

16 Claims, 1 Drawing Sheet

(56) References Cited

U.S. PATENT DOCUMENTS

| | | | |
|---|---|---|---|
| 7,001,413 B2* | 2/2006 | Butler | 607/88 |
| 7,217,266 B2* | 5/2007 | Anderson et al. | 606/12 |
| 7,282,060 B2* | 10/2007 | DeBenedictis et al. | 607/88 |
| 7,309,335 B2* | 12/2007 | Altshuler et al. | 606/11 |
| 7,544,163 B2* | 6/2009 | MacKinnon et al. | 600/178 |
| 7,720,306 B2* | 5/2010 | Gardiner et al. | 382/276 |
| 7,824,395 B2* | 11/2010 | Chan et al. | 606/10 |
| 7,831,017 B2* | 11/2010 | Myles | 378/65 |
| 7,918,796 B2* | 4/2011 | Nycz et al. | 600/439 |
| 7,988,688 B2* | 8/2011 | Webb et al. | 606/13 |
| 7,993,289 B2* | 8/2011 | Quistgaard et al. | 601/2 |
| 8,033,284 B2* | 10/2011 | Porter et al. | 128/898 |
| 8,092,447 B2* | 1/2012 | Dolleris | 606/13 |
| 8,235,530 B2* | 8/2012 | Maad | 353/28 |
| 8,308,642 B2* | 11/2012 | Zhou et al. | 600/306 |
| 2002/0002330 A1* | 1/2002 | Vilsmeier | 600/407 |
| 2002/0023652 A1* | 2/2002 | Riaziat et al. | 128/897 |
| 2002/0065461 A1* | 5/2002 | Cosman | 600/426 |
| 2002/0133144 A1* | 9/2002 | Chan et al. | 606/4 |
| 2004/0002641 A1* | 1/2004 | Sjogren et al. | 600/407 |
| 2004/0158300 A1* | 8/2004 | Gardiner | 607/88 |
| 2005/0143793 A1* | 6/2005 | Korman et al. | 607/94 |
| 2005/0195587 A1* | 9/2005 | Moctezuma De La Barrera et al. | 362/5 |
| 2005/0265516 A1* | 12/2005 | Haider | 378/20 |
| 2006/0030908 A1* | 2/2006 | Powell et al. | 607/88 |
| 2006/0079757 A1* | 4/2006 | Smith et al. | 600/416 |
| 2006/0116669 A1* | 6/2006 | Dolleris | 606/17 |
| 2007/0253614 A1* | 11/2007 | Jung et al. | 382/131 |
| 2008/0015553 A1* | 1/2008 | Zacharias | 606/4 |
| 2008/0033410 A1* | 2/2008 | Rastegar et al. | 606/9 |
| 2008/0033412 A1* | 2/2008 | Whelan et al. | 606/11 |
| 2008/0051773 A1* | 2/2008 | Ivanov et al. | 606/12 |
| 2008/0065056 A1* | 3/2008 | Powell et al. | 606/9 |
| 2008/0091249 A1* | 4/2008 | Wang | 607/88 |
| 2008/0240353 A1* | 10/2008 | Myles | 378/65 |
| 2009/0029310 A1* | 1/2009 | Pumphrey et al. | 433/24 |
| 2009/0153837 A1* | 6/2009 | Wang et al. | 356/43 |
| 2011/0183304 A1* | 7/2011 | Wallace et al. | 434/234 |
| 2012/0045742 A1* | 2/2012 | Meglan et al. | 434/268 |
| 2012/0095533 A1* | 4/2012 | Wang | 607/89 |
| 2012/0194814 A1* | 8/2012 | Wang | 356/301 |

OTHER PUBLICATIONS

Wheeland R.G., Clinical Uses of Lasers in Dermatology, Lasers in Surgery and Medicine 162-23 (1995).*

Tanghetti E. & Gillis P., Photometric and clinical assessment of localized UVB phototherapy systems for the high-dosage treatment of stable plaque psoriasis, J Cosmetic & Laser Ther 2003; 5: 101-106.*

* cited by examiner

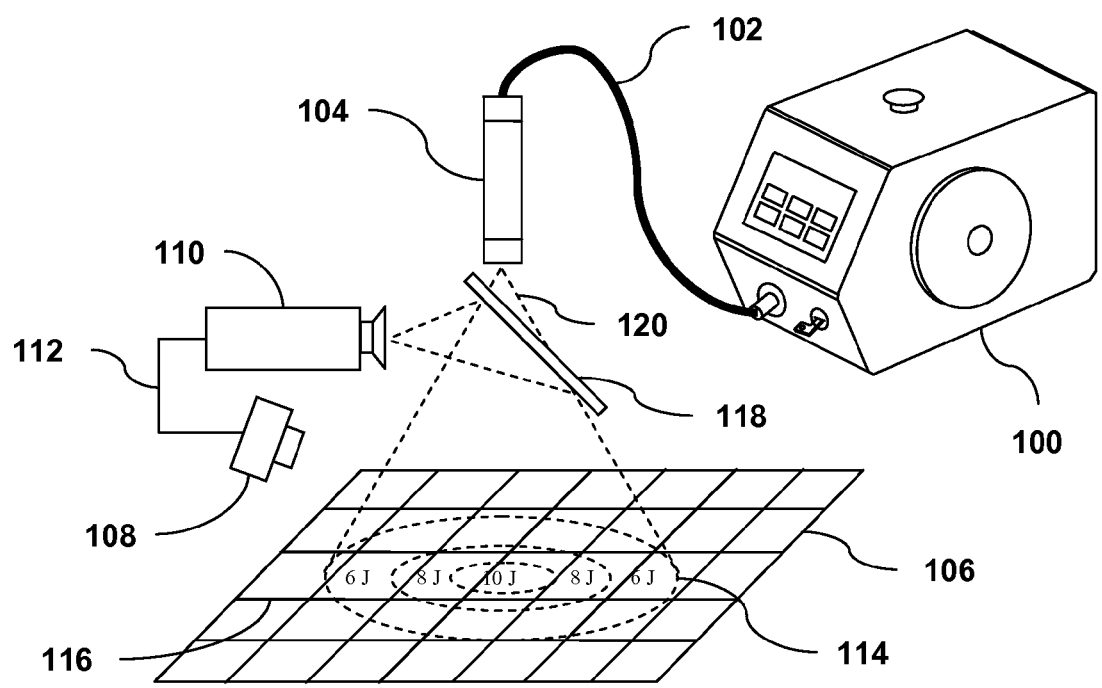

PRECISELY GUIDED PHOTOTHERAPY APPARATUS

REFERENCE TO RELATED APPLICATION

This application claims an invention which was disclosed in Provisional Patent Application No. 61/309,671, filed Mar. 2, 2010, entitled "PRECISELY GUIDED PHOTOTHERAPY APPARATUS". The benefit under 35 USC §119(e) of the above mentioned United States Provisional Applications is hereby claimed, and the aforementioned application is hereby incorporated herein by reference.

FIELD OF THE INVENTION

This invention generally relates to a phototherapy apparatus, and more specifically to a precisely guided phototherapy apparatus.

BACKGROUND

Phototherapy is a medical and veterinary technique which uses lasers, light emitting diodes (LEDs) or other types of light sources to stimulate or inhibit cellular function. Recently, this technique has been widely used for treating soft tissue injury, chronic pain, and promoting wound healing for both human and animal targets.

Typically, the phototherapy procedure involves radiating light energy in the ultraviolet (UV), visible, or infrared wavelength onto or into the patient's skin. It is highly desirable to precisely control the dose of light energy that is applied on a specific treatment area to achieve an optimum therapeutic effect. However, none of the existing phototherapy apparatuses could fulfill this task due to the following reasons. First, the therapeutic light generally has a non-uniform beam profile, i.e. the light intensity varies significantly from the center to the edge of the light beam. Thus the treatment area inevitably receives uneven energy dosages. Second, some therapeutic light (e.g. the infrared light) is invisible to the human eyes. In these cases, an aiming beam in the visible wavelength is generally provided to guide the therapeutic light. However, due to their wavelength and power difference, the aiming beam generally has an intensity profile different from that of the therapeutic light, which prevents it from providing precise dosage guidance to the clinician or practitioner. Third, the practitioner or clinician usually needs to scan the therapeutic light beam to cover a large treatment area, making it even harder to track the exact delivered energy dosage for any specific region of the area.

There thus exists a need for an improved phototherapy apparatus, which can provide real time monitoring of the delivered light energy dosage on the subject surface of the patient for assisting the practitioner or clinician in precisely controlling the phototherapy procedure.

SUMMARY OF THE INVENTION

It is the overall goal of the present invention to solve the above mentioned problems and provide a precisely guided phototherapy apparatus. The phototherapy apparatus comprises sensor means for monitoring the intensity, position, and movement of the therapeutic light beam over the treatment area. The delivered light energy dosage is determined accordingly based on these parameters. The phototherapy apparatus further comprises a projector device for projecting markers on top of the treatment area. The markers represent the values of the delivered light energy dosage for assisting the practitioner or clinician in precisely controlling the phototherapy procedure.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1 illustrates one exemplary embodiment of the precisely guided phototherapy apparatus.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a precisely guided phototherapy apparatus. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1 illustrates one exemplary embodiment of the precisely guided phototherapy apparatus. Here the light source module 100 of the phototherapy apparatus comprises a high power diode laser operating at a near infrared wavelength of 980 nm. The output power of the diode laser is adjustable in the range of 0.5-15 watts for producing photochemical reaction, e.g. up-regulation and down-regulation of adenosine triphosphate (ATP), reactive oxygen species, and nitric oxide in the subject biological tissue 106. The photochemical reaction in turn produces the following therapeutic effects: (i) stimulating white blood cell activity; (ii) accelerating macrophage activity, growth factor secretion and collagen synthesis; (iii) promoting revascularization and micro-circulation; (iv) increasing fibroblast numbers and collagen production; (v) accelerating epithelial cell regeneration and speeding up wound healing; (vi) increasing growth-phasespecific DNA synthesis; (vii) stimulating higher activity in cell proliferation and differentiation; (viii) increasing the intra and inter-molecular hydrogen bonding. All these therapeutic effects combine to benefit the subject biological tissue 106.

Referring to FIG. 1, the phototherapy apparatus comprises an optical fiber 102 and an output wand 104 for delivering the laser light from the light source module 100 onto the surface of the subject biological tissue 106. The laser light 120 is absorbed by the chromophores (e.g. water, melanin, hemoglobin) of the biological tissue to trigger the above disclosed photochemical reactions. The phototherapy apparatus further comprises an image sensor 108, e.g. a CCD or CMOS image sensor for capturing successive images of the subject surface. These images record the position and intensity profile of the therapeutic light on the surface of the biological tissue 106. Variations between successive images are processed by an image processing unit (not shown) and translated into movement of the therapeutic light beam over the treatment area. Based on the recorded intensity, position, and movement information of the therapeutic light beam, the delivered light energy dosage for each specific region of the treatment area (hence an energy dosage distribution) is determined. Through connection 112, the energy dosage distribution information is transmitted to a digital light projector 110, e.g. a DLP (digital light processing), LCD (liquid crystal display) or LCOS (liquid crystal on silicon) projector, which projects corresponding markers 114 onto the surface of the biological tissue. The markers 114 can be numeral values or colored graphics representing the delivered light energy dosage. For example, a green color may represent an energy dosage within an appropriate range, while a yellow color and a red color may represent energy dosages below and above appropriate level, respectively. The practitioner or clinician can precisely control the phototherapy procedure based on the guidance of the projected markers 114.

In this exemplary embodiment, the output wand 104 and the projector 110 share the same optical path with their output light beams combined by a beam combiner 118 (e.g. a dichroic beam combiner). Thus the projected markers 114 coincide with the laser beam 120 on the subject surface. The digital light projector 110 may further project a visible image of the intensity profile of the laser beam 120 (e.g. a contour image with different intensity levels displayed in different colors) onto the surface of the biological tissue 106. The visible image coincides with the infrared laser beam such that its intensity, position, and movement are revealed to the practitioner or clinician. The values of the intensity profile, as well as the energy dosage distribution, can be displayed on top of the visible image. A plurality of grids 116, either in the form of a transparent grid paper, or projected lines from the light projector 110, may be introduced on top of the subject surface to facilitate tracking of the therapeutic light beam. The output wand 104, the image sensor 108, and the light projector 110 of the present embodiment can be integrated together to form a common outputting/sensing/projecting port for the phototherapy apparatus. Before the phototherapy procedure, the light projector 110 may display a simulated or pre-recorded laser beam profile in accordance to the selected laser parameters (e.g. output power of the laser, distance from the output wand to the tissue), which assists the practitioner/clinician in optimizing the treatment procedure.

In a simplified variation of the present embodiment, the digital light projector 110 may be replaced with a laser or LED pointer, which projects different colored light onto the subject surface. The color varies in accordance to the delivered light energy dosage for assisting the practitioner/clinician with energy dosage control. The image sensor 108 may be replaced with a plurality of photo detectors for recording the intensity, position, and movement of the therapeutic light beam. Alternatively, the position and movement of the output wand 104 (hence the position and movement of the therapeutic light beam) can be tracked with other types of sensors, such as thermal, mechanical, electrical, magnetic, or acoustic sensors.

In another variation of the present embodiment, the phototherapy apparatus further comprises a temperature sensor, preferably in the form of a non-contact infrared temperature sensor for monitoring the temperature of the subject biological tissue. Through the light projector, the measured temperature value is projected onto the surface of the biological tissue as a means to control the light energy dosage.

In yet another variation of the present embodiment, the phototherapy apparatus may comprise multiple laser sources with different output wavelengths to treat biological tissues with different type and concentration of chromophores. The outputs of the multiple laser sources can be combined at adjustable proportions and simultaneously applied to the biological tissue to achieve an enhanced treatment result. The laser sources may operate in a pulsed mode such that a high peak power is produced to increase the penetration depth of the laser light and/or to trigger nonlinear photochemical reactions yet the average power of the laser light is maintained at low levels to avoid any tissue damage.

The disclosed phototherapy apparatus can be used in other fields as well, such as photo-dynamic therapy, where the light source is used to activate a photosensitizing drug, or in aesthetic treatments such as acne treatment, wrinkle removal, skin-tightening, etc.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A phototherapy apparatus for treating biological tissue, said phototherapy apparatus comprising:

at least one light source configured to produce therapeutic light to be delivered onto a surface of the biological tissue;

a sensor and processing unit configured to monitor intensity, position, and movement of said therapeutic light over the surface of the biological tissue and to determine a delivered light energy dosage distribution of the therapeutic light based on said intensity, position, and movement of said therapeutic light and to transmit the delivered light energy dosage distribution to a light projector device in communication with said sensor, said light projector device configured to project visible markers representing values of said delivered light energy dosage distribution onto the surface of the biological tissue.

2. The phototherapy apparatus of claim 1, wherein said markers comprise numerals.

3. The phototherapy apparatus of claim 1, wherein said markers comprise graphics.

4. The phototherapy apparatus of claim 1, wherein said markers have different colors.

5. The phototherapy apparatus of claim 1, wherein said sensor comprises optical, thermal, mechanical, electrical, magnetic, or acoustic sensors.

6. The phototherapy apparatus of claim 1, wherein said sensor comprises an image sensor.

7. The phototherapy apparatus of claim 6, wherein said image sensor comprises a CCD or CMOS image sensor.

8. The phototherapy apparatus of claim 1, wherein said at least one light source comprises a near infrared laser.

9. The phototherapy apparatus of claim 1, wherein said at least one light source comprises a visible laser.

10. The phototherapy apparatus of claim 1, wherein said at least one light source comprises an ultraviolet laser.

11. The phototherapy apparatus of claim 1, wherein said light projector device comprises a digital light projector.

12. The phototherapy apparatus of claim 1, wherein said light projector device comprises a laser or light emitting diode (LED) pointer.

13. The phototherapy apparatus of claim 1, wherein said light projector device is configured to project a visible image of an intensity profile of said therapeutic light onto the surface of the biological tissue, wherein said visible image coincides with said therapeutic light on the surface of the biological tissue.

14. The phototherapy apparatus of claim 13, wherein said light projector device is configured to project markers representing values of said intensity profile on top of said visible image.

15. The phototherapy apparatus of claim 1, further comprising a temperature sensor for measuring a temperature of the biological tissue, wherein said light projector device projects markers representing the measured temperature value onto the surface of the biological tissue.

16. A phototherapy method for treating biological tissue, said phototherapy method comprising the steps of:
providing the phototherapy apparatus of claim 1
applying said therapeutic light onto the surface of the biological tissue;
monitoring intensity, position, and movement of said therapeutic light over the surface of the biological tissue and determining a delivered light energy dosage distribution of the therapeutic light based on said intensity, position, and movement of said therapeutic light and transmitting the delivered light energy dosage distribution to the light projector device, and projecting visible markers representing values of said delivered light energy dosage distribution onto the surface of the biological tissue.

\* \* \* \* \*